(12) United States Patent  
Hoshino et al.

(10) Patent No.: US 7,400,705 B2  
(45) Date of Patent: Jul. 15, 2008

(54) METHOD OF EVALUATING ION-EXCHANGE FILM, METHOD OF EVALUATING ORGANIC SAMPLE AND X-RAY MEASURING APPARATUS

(75) Inventors: Kazuhito Hoshino, Saitama (JP); Yoshio Iwasaki, Tokyo (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 0 days.

(21) Appl. No.: 10/456,508

(22) Filed: Jun. 9, 2003

(65) Prior Publication Data

US 2004/0008815 A1    Jan. 15, 2004

(30) Foreign Application Priority Data

Jun. 19, 2002    (JP)    ............................. 2002-178359

(51) Int. Cl.  
*G01N 23/201*    (2006.01)

(52) U.S. Cl. .............................. 378/86; 378/80; 378/87; 378/88

(58) Field of Classification Search .................. 378/80, 378/86–89; 250/304  
See application file for complete search history.

(56) References Cited

U.S. PATENT DOCUMENTS

| | | | | |
|---|---|---|---|---|
| 5,805,662 A * | 9/1998 | Kurbatov et al. | ............... | 378/87 |
| 5,923,720 A * | 7/1999 | Barton et al. | .................. | 378/84 |
| 6,011,074 A * | 1/2000 | Sorenson et al. | .............. | 521/26 |
| 6,054,712 A * | 4/2000 | Komardin et al. | ....... | 250/363.06 |
| 6,330,301 B1 * | 12/2001 | Jiang | ........................... | 378/85 |
| 6,503,711 B1 * | 1/2003 | Krull et al. | ....................... | 435/6 |
| 6,504,902 B2 | 1/2003 | Iwasaki et al. | | |
| 6,895,075 B2 * | 5/2005 | Yokhin et al. | ................. | 378/90 |
| 6,908,671 B2 * | 6/2005 | Hosokawa et al. | .... | 428/355 AC |

(Continued)

FOREIGN PATENT DOCUMENTS

JP         03218448 A  *  9/1991

(Continued)

OTHER PUBLICATIONS

Kazuhito Hoshino et al., Copending U.S. Appl. No. 10/457,354, filed Jun. 10, 2003.

(Continued)

*Primary Examiner*—Edward J. Glick  
*Assistant Examiner*—Thomas R. Artman  
(74) *Attorney, Agent, or Firm*—Buchanan Ingersoll & Rooney PC

(57) ABSTRACT

Disclosed herein is a method of evaluating the performance of an ion-exchange film. In the method, small-angle scattering curves for the ion-exchange film at different humidities are obtained by an X-ray measuring apparatus that can detect X-rays scattered at small angles with respect to the axis of an X-ray applied to the ion-exchange film. From the positions of the peaks on the small-angle scattering curves and the X-ray intensities at these peaks, the change in the characteristic of the film, which accompanies change in the molecular structure (hence, ion-exchanging ability) of the ion-exchange film due to the change in humidity, is evaluated. The humidity ambient to the ion-exchange film can be adjusted by a humidity-adjusting device that comprises a vapor source, gas source, gas mixer and gas-introducing pipe.

4 Claims, 12 Drawing Sheets

U.S. PATENT DOCUMENTS 6,937,695 B2 * 8/2005 Hoshino .................. 378/86
6,993,113 B2 * 1/2006 Hoshino et al. ............ 378/86
2004/0008816 A1 * 1/2004 Hoshino et al. ............ 378/86

FOREIGN PATENT DOCUMENTS

JP        2001-356197 A    12/2001

OTHER PUBLICATIONS

J.A. Elliott et al., "Interpretation of the Small-Angle X-ray Scattering from Swollen and Oriented Perfluorinated Ionomer Membranes", *Macromolecules*, vol. 33, No. 11, 2000, pp. 4161-4171, American Chemical Society, Washington, D.C. USA.

R. Mosdale et al., "Water Profile Determination in a Running Proton Exchange Membrane Fuel Cell Using Small-Angle Neutron Scattering", *Journal of Membrane Science*, vol. 118, 1996, pp. 269-277, Elsevier Scientific Publishing Company, Amsterdam, NL.

G. Gebel, "Structural Evolution of Water Swollen Perfluorosulfonated Ionomers From Dry membrane to Solution", *Polymer* vol. 41, No. 15, Jul. 2000, pp. 5829-5838, Elsevier Science Publishers B.V., Great Britain.

P.J. James et al, "In situ Rehydration of Perfluorosulphonate Ion-Exchange Membrane Studied by AFM", *Polymer* vol. 41, No. 11, 2000, pp. 4223-4231, Elsevier Science Publishers B.V., Great Britain.

A. Okawara et al., "Real-time analysis of small-angle X-ray scattering from perfluorocarboxylic ionomer membranes during electrodialysis," Polymer 1992, vol. 33, No. 8, Elsevier, pp. 1579-1582.

Abstract of Soviet Union Patent No. 1582097, Crystallography DES, Jul. 30, 1990, from Database WPI, Section EI, Week 199113, AN 1991-093510, Derwent Publications Ltd., London, GB.

T.D. Gierke et al., "The Morphology in Nafion Perfluorinated Membrane Products, as Determined by Wide-and Small-Angle X-Ray Studies," Journal of Polymer Science: Polymer Physics Edition, 1981, vol. 19, No. 11, John Wiley & Sons, Inc., New York, pp. 1687-1704.

* cited by examiner

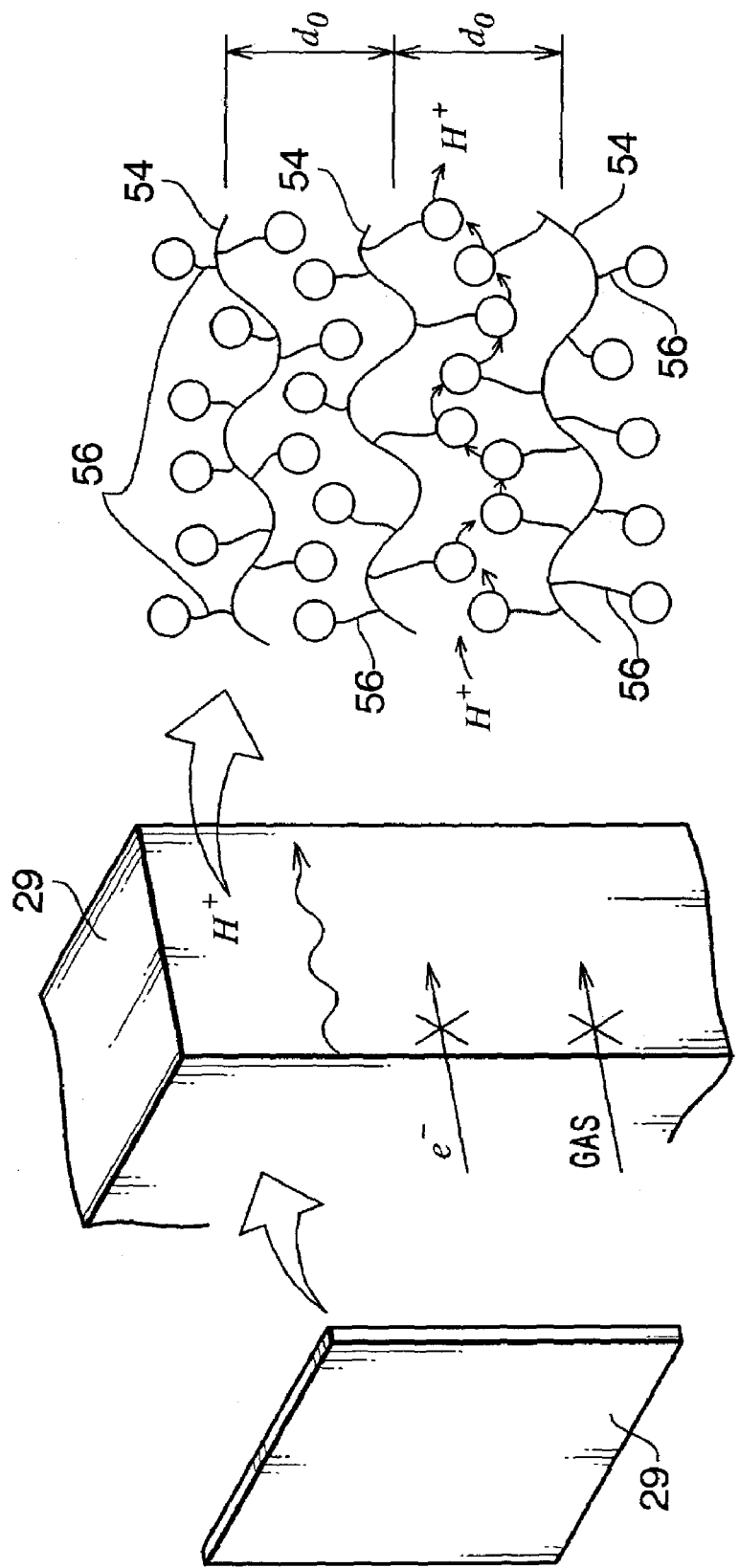

METHOD OF EVALUATING ION-EXCHANGE FILM, METHOD OF EVALUATING ORGANIC SAMPLE AND X-RAY MEASURING APPARATUS

BACKGROUND OF THE INVENTION

1. Field of the Invention

The present invention relates to a method of evaluating the performance of organic samples, such as ion-exchange film. The invention also relates to an X-ray measuring apparatus that is fit for use in this method.

2. Description of the Related Art

Recently, various apparatuses including macromolecular organic materials are provided in the industry. In the field of fuel cells, for example, the main component of the fuel cell is an ion-exchange film that is made of macromolecular organic material. As FIG. 12 shows, the fuel cell comprises a pair of electrodes, or fuel pole 51 and air pole 52, and an ion-exchange film 29 interposed between the poles 51 and 52. Hydrogen ($H_2$), i.e., the fuel, is supplied through the fuel pole 51 to the ion-exchange film 29. Also, oxygen ($O_2$) is supplied through the air pole 52 to the ion-exchange film 29.

In the fuel cell, hydrogen and oxygen undergo the following chemical reaction:

$$2H_2 + O_2 \rightarrow 2H_2O + \text{electric energy} + \text{heat}$$

This is a chemical reaction that is invert to the electrolysis of water, resulting in obtaining electric energy. The heat generated along with the electric energy can be absorbed by an appropriate cooling method, for example, a method in which cooling water is circulated around.

The ion-exchange film 29 used in the fuel cell has been made by synthesizing straight chains 54 and side chains 56. The straight chains 54 are spaced from one another at interval d0. The side chains 56 branch from the straight chains 54. In Nafion (registered trademark of E.I. du Pont de Nemours and Co.) known widely as an ion-exchange film, the straight chains 54 and the side chains 56 have such molecular structures as specified in FIG. 11.

In these molecular structures, the straight chains 54 are Teflon (registered trademark) groups and the side chains 56 are those formed by combining functional groups. Some of the functional groups shown in FIG. 11 may be removed or substituted by other functional groups, or other functional groups may be added, to alter the molecular structure of the ion-exchange film. The performance of the ion-exchange film can thereby be changed in various ways.

Having this specific molecular structure, the ion-exchange film 29 allows the passage of protons $H^+$ and does not allow the passage of electrons $e^-$ and gas, as illustrated in FIG. 10B. Namely, the film 29 performs ion exchange. The higher the ion-exchanging performance is, the higher the performance of the fuel cell is. The ion-exchanging performance is considered to change in accordance with the molecular structure shown in FIG. 10C. More specifically, it is influenced by the interval d0 between the straight chains, the arrangement of the side chains 56, and the like.

Hence, it is recommended that the molecular structure of ion-exchange film or the like, which is made of macromolecular organic material, be determined in order to evaluate performance of the macromolecular organic material. Methods of determining the molecular structures of macromolecular organic materials are known. Among these methods are the NMR-measuring method and the IR-measuring method. In the NMR method, an NMR (Nuclear Magnetic Resonance) spectrometer is employed. In the IR method, an IR (Infrared) spectrophotometer is used.

The NMR-measuring method utilizes the phenomenon called "nuclear magnetic resonance," in which the amplitude of magnetic moment changes when an electromagnetic wave is applied to an atom whose nuclear has magnetic moment, in order to determine the molecular structure, etc. of a sample. The IR-measuring method determines the molecular structure, etc. of a sample, from the infrared absorption spectrum, i.e., the relation between the intensity of the infrared beam passing the sample (plotted on the ordinate) and the wavelength of the infrared beam (plotted on the abscissa).

With the NMR-measuring method and the IR-measuring method, however, it is difficult to obtain reliable evaluation of the sample, by using a measuring apparatus of simple configuration. Further, they cannot determine the molecular structure of macromolecular organic materials such as ion-exchange film, while maintaining the materials at such high humidity and such high temperature, as they are set when they are used in practice. This is why macromolecular organic materials, such as ion-exchange film, are not evaluated by means of in-situ measuring at present. In other words, the materials are not evaluated for their molecular structures in the very conditions they are used.

SUMMARY OF THE INVENTION

The present invention has been made in view of the foregoing. A first object of the invention is to provide a method that can reliably accurately determine the molecular structure of macromolecular organic materials, such as ion-exchange film, by using apparatus that are widely and generally employed. A second object of this invention is to provide a method that can determine the molecular structure of such a material by in-situ measuring, particularly at a changing humidity.

To achieve the aforesaid objects, a method of evaluating the performance of an ion-exchange film, according to the invention comprises the steps of: changing humidity ambient to the ion-exchange film; and obtaining small-angle scattering curves for the ion-exchange film at different humidities, by means of an X-ray measuring apparatus which is configured to detect X-rays scattered at small angles with respect to the axis of an X-ray applied to the ion-exchange film.

The small-angle scattering curves are curves G that are shown in FIG. 7. Each curve G is formed by plotting the scattering angle (2θ) on the abscissa, and the X-ray intensity on the ordinate, as seen from FIG. 7. The curves H shown in FIG. 8 are also small-angle scattering curves.

The aforesaid method of evaluating the ion-exchange film can reliably determine the molecular structure of the ion-exchange film, merely by using an ordinary X-ray measuring apparatus that is widely and generally employed. The X-ray measuring apparatus is more versatile than the NMR-measuring apparatus and the IR-measuring apparatus, in respect of the installation of additional devices for the sample. Thus, the method can determine the molecular structure of the sample in the same conditions as the sample is actually used.

The method described above comprises the step of changing humidity ambient to the ion-exchange film. Therefore, the sample can be subjected to in-situ measuring, or evaluated in the very condition it is used in practice. For example, the ability the ion-exchange film exhibits while wetted as shown in FIG. 7 and the ability the film exhibits while dried as shown in FIG. 8 can be determined. Namely, the method can detect the change in the performance of the ion-exchange film.

It is desired that the method described above comprises the step of finding a difference between the positions of peaks on the small-angle scattering curves and/or a difference between the X-ray intensities at the peaks. The visual sense of an observer or the arithmetic unit of a computer may perform this step.

The difference between the positions of peaks on the small-angle scattering curves for a plurality of ion-exchange films may be obtained. Then, the molecular structures of the respective films can be determined. From the molecular structures of the films, the difference in performance between the ion-exchange films can be evaluated.

Further, once the difference between the intensity of peaks on the small-angle scattering curves for a plurality of ion-exchange films are determined, it is possible to verify the number of side chains and the regularity of the molecular structure of each ion-exchange film. Thus, the difference in performance between the ion-exchange films can be evaluated.

In the method of evaluating an ion-exchange film, it is desirable to perform the step of changing humidity ambient to the ion-exchange film, by inserting the ion-exchange film into a sample chamber and applying gas having humidity into the sample chamber. In this case, it is desired that the sample chamber be airtight, except for the part where gas flows. This makes it easy to set the ion-exchange film at a humidity desired.

In the method described above, it is desired that the step of obtaining small-angle scattering curves should have a step of obtaining a two-dimensional scattering profile pertaining to the ion-exchange film, by using a two-dimensional X-ray detector.

The two-dimensional X-ray detector is of the type that receives X-rays in a plane and detects X-rays at any points in the plane. It may be an X-ray detector having an X-ray dry plate or X-ray film, or may be an X-ray detector having a storage phosphor. Alternatively, it may be an X-ray detector that incorporates a planer CCD (Charge Coupled Device) sensor. Storage phosphor is energy-accumulating phosphor, which is made by applying fine crystals of super-luminance material, such as $BaFBr:Er^{2+}$ on the surface of a flexible film, plate-like film or any other member. The storage phosphor can store electromagnetic waves, such as X-rays, in the form of energy. When irradiated with emission stimulating light, such as a laser beam, the storage phosphor releases the energy in the form of light.

That is, when X-rays or the like is applied to the storage phosphor, energy is accumulated, as a latent image, in that part of the storage phosphor which has been irradiated with the X-rays. When the storage phosphor is irradiated with a laser beam or the like, it releases the energy of the latent image in the form of light. The light released may be detected by a photoelectric transducer, such as a photoelectric tube. Thus, the diffraction angle and intensity of the X-rays that have formed the latent image can be measured.

The CCD sensor is an electronic element known in the art. It is an X-ray detector that comprises CCDs (i.e., Charge Coupled Devices) arranged in a row or in a planar matrix. The CCD has a plurality of electrodes on an insulating layer that is provided on, for example, a silicon substrate. The electrodes are arranged in a row or in rows and columns, thus forming an electrode array. The CCD sensor is constructed by arranging the electrode array correspondingly for portions for receiving X-rays.

When X-rays are applied to the respective electrodes of the array, an electric charge is accumulated beneath each electrode. When a voltage is applied between the electrode and the substrate, the electric charge is transferred in the CCD sensor until it is output from the CCD sensor. Thus, the CCD sensor can detect the positions where the X-rays have applied to the electrodes and the intensities of the X-rays, almost at the same time.

The two-dimensional scattering profile is such a two-dimensional image as shown in FIG. 9A or FIG. 9B. These images are formed on the X-ray receiving surface of the two-dimensional X-ray detector when the surface is exposed with X-rays generated from the ion-exchange film, i.e., the sample. The small-angle scattering curves G shown in FIG. 7 and the small-angle scattering curves H shown in FIG. 8 are obtained by plotting values in the graph. Each of these values has been acquired by integrating the regions for the same scattering angle ($2\theta$), which exist in the two-dimensional scattering profile E shown in FIG. 9A or 9B.

In the above-described method of evaluating an ion-exchange film, it is desirable that the X-ray measuring apparatus should have an X-ray focusing means which is arranged on a propagation path of the X-ray applied to the ion-exchange film. Note that the X-ray focusing means is an X-ray optical element that can focus an X-ray diverging while propagating, at a downstream point. The X-ray focusing element may be, for example, a con-focal mirror that utilizes the reflection of the X-ray, or an X-ray focusing element that makes use of the diffraction of the X-ray.

In any X-ray optical system of ordinary type that has no X-ray focusing means, the X-rays applied to an ion-exchange film, or the sample, have low intensity. An X-ray focusing means, if used as in the method described above, can focus and intensify X-rays. Thus, high-intensity X-rays can be applied to the ion-exchange film in the method according to this invention.

Any X-ray measuring apparatus of the ordinary structure, wherein the X-rays used have low intensity. Therefore, it needs a very long time to obtain such a two-dimensional scattering profile E as shown in FIG. 9A or 9B and, hence, to obtain such small-angle scattering curves G as illustrated in FIG. 7. In contrast, the X-ray measuring apparatus described above can obtain a two-dimensional scattering profile E within a very short time, because it comprises the X-ray focusing means that can apply a high-intensity X-ray to the ion-exchange film. This helps to perform in-situ measuring on the ion-exchange film.

When the ion-exchange film is subjected to the in-situ measuring, the film immerses in liquid, for example, water, is thereby wetted, and then is heated to a high temperature such as 90° C. Since water thus heated up to about 90° C. quickly changes in state, or is vaporized, the ion-exchange film cannot be subjected to the in-situ measuring if it takes a long time to measure the small-angle scattering of X-rays.

In the method of evaluating an ion-exchange film according to the present invention, the ion-exchange film can be irradiated with a high-intensity X-ray. Therefore, the method can reliably evaluate ion-exchange films that can remain in the same condition, but for a very short time.

In the method of evaluating an ion-exchange film according to the present invention, it is desired that the X-ray focusing means be a con-focal mirror. Note that a con-focal mirror is an X-ray reflecting mirror that has at least two X-ray reflecting surfaces intersecting with each other at right angles. The mirror is so designed that the X-rays reflected from the X-ray reflecting surfaces meet at the same focal point.

In the method of evaluating an ion-exchange film, which comprises X-ray focusing means, it is desired that the X-ray measuring apparatus should further have a point-focus X-ray source.

The term "point focus" is used in contrast to "line focus." "Point focus" pertains to X-rays that have a square cross section having four sides of substantially the same length, forming a square light spot on the sample. By contrast, the term "line focus" pertains to X-rays that have a rectangular cross section, thus forming an elongated light spot on the sample. The point-focus X-ray source emits X-ray beams, each forming, on the sample, a circular light spot having a diameter of, for example, about 0.3 mm or a square light spot having a size of about 0.3 mm×about 0.3 mm.

If a line-focus X-ray source is used, those parts of the rectangular light spot which lie outside each tiny light-receiving region of the ion-exchange film will be wasted, not contributing to the measuring of the X-ray. This means that the line-focus X-ray source cannot apply sufficiently intense X-rays to the ion-exchange film. By contrast, any X-ray emitted from the point-focus X-ray source is applied, in its entirety, to one tiny light-receiving region of the ion-exchange film. Thus, the point-focus X-ray source can apply sufficiently intense X-rays to the ion-exchange film.

A method of evaluating the performance of an organic sample, according to the present invention, comprises the steps of: changing humidity ambient to the organic sample; and obtaining small-angle scattering curves for the organic sample at different humidities, by means of an X-ray measuring apparatus which is configured to detect X-rays scattered at small angles with respect to the axis of an X-ray applied to the organic sample. Note that the organic sample may be a drug, a genome-pharmaceutical substance, a synthesized compound, or the like, to say nothing of an ion-exchange film.

This method of evaluating an organic sample can accurately determine the molecular structure of the organic sample, merely by using an X-ray measuring apparatus that is generally and widely used. Further, the method can analyze the molecular structure of the organic sample in the same conditions as the sample is actually used. This is because the X-ray measuring apparatus is more versatile than the NMR-measuring apparatus and the IR-measuring apparatus, in respect of the installation of additional devices for the sample.

The method of evaluating an organic sample, described above, comprises the step of changing humidity ambient to the organic sample. Thus, in-situ measuring can be performed on the organic sample. That is, the sample can be measured, while its ambient humidity is being changed in the same way as it is used in practice.

It is desired that the method of evaluating an organic sample, described above, should comprise the step of finding a difference between the positions of peaks on the small-angle scattering curves and/or a difference between the X-ray intensities at the peaks.

Once the difference in the peak positions on the small-angle scattering curves, between a plurality of organic samples is obtained, the molecular structures of the organic samples can be analyzed. Then, the difference in characteristic between the samples can be evaluated. If the difference in X-ray intensities at the peaks, between the organic samples, is obtained, it will be possible to verifying the number of side chains and the regularity of the molecular structure. In this case, the difference in characteristic between the organic samples can be evaluated.

In the method of evaluating an organic sample, described above, it is desired that the step of changing humidity ambient to the ion-exchange film be carried out by inserting the organic sample into a sample chamber and applying gas having humidity into the sample chamber. In this case, it is desired that the sample chamber be airtight, except for the part where gas flows. This makes it easy to set the ion-exchange film under a desirable humidity.

In the method of evaluating an organic sample, described above, it is desired that the step of obtaining small-angle scattering curves should have a step of obtaining a two-dimensional scattering profile pertaining to the organic sample, by using a two-dimensional X-ray detector. Once such a two-dimensional scattering profile E as shown in FIG. 9A or 9B is obtained, the difference in molecular structure between the organic samples and, hence, the difference in performance between them can be determined.

In the method of evaluating an organic sample, described above, it is desired that the X-ray measuring apparatus has an X-ray focusing means which is arranged on a propagation path of the X-ray applied to the organic sample. Then, the organic sample can be irradiated with high-intensity X-rays. This renders it possible to carry out reliable evaluation on organic samples that can remain in the same condition, but for a short time.

In the method of evaluating an organic sample, described above, the X-ray focusing means may comprise a con-focal mirror. If a con-focal mirror is employed, the X-ray can be focused before it is applied to the organic sample. Then, the organic sample can be irradiated with high-intensity X-rays. As a result, a two-dimensional scattering profile pertaining to the organic sample can be obtained within a very short time. This helps much to accomplish in-situ measuring of the organic sample.

In the method of evaluating an organic sample, described above, it is desired that the X-ray measuring apparatus should further have a point-focus X-ray source. A point-focus X-ray source emits X-rays, each having a cross section that is almost square. The X-ray focusing means can focus such an X-ray at a tiny light-receiving region of the organic sample. Thus, the point-focus X-ray source can apply sufficiently intense X-rays to the organic sample.

An X-ray measuring apparatus according to the present invention comprises: a small-angle X-ray optical system which is configured to detect X-rays scattered at small angles with respect to the axis of an X-ray applied to a sample; means for calculating the positions of peaks on the small-angle scattering curves obtained by using the small-angle X-ray optical system; and means for displaying the position of peaks thus calculated together with the small-angle scattering curves. The X-ray measuring apparatus can determine the positions of peaks on the small-angle scattering curves, very easily and accurately. Thus, the apparatus can evaluate the sample with ease and at high speed.

It is desired that the X-ray measuring apparatus should further comprises: a sample chamber for holding the sample and allowing passage of X-rays; and a humidity-adjusting means for changing the humidity in the sample chamber. Then, the X-ray measuring apparatus can change the humidity ambient to the sample as is desired. The apparatus can therefore perform in-situ measuring on materials that are used at changing humidity.

BRIEF DESCRIPTION OF THE DRAWINGS

FIG. 10 is a schematic diagram illustrating the molecular structure of ion-exchange film;

DETAILED DESCRIPTION OF THE PREFERRED EMBODIMENTS

First Embodiment

An embodiment of a method of evaluating ion-exchange film, or an organic sample, and an embodiment of an X-ray measuring apparatus, both according to the present invention, will be described. These are no more than examples of this invention, which is not limited to these embodiments.

Figure 1:
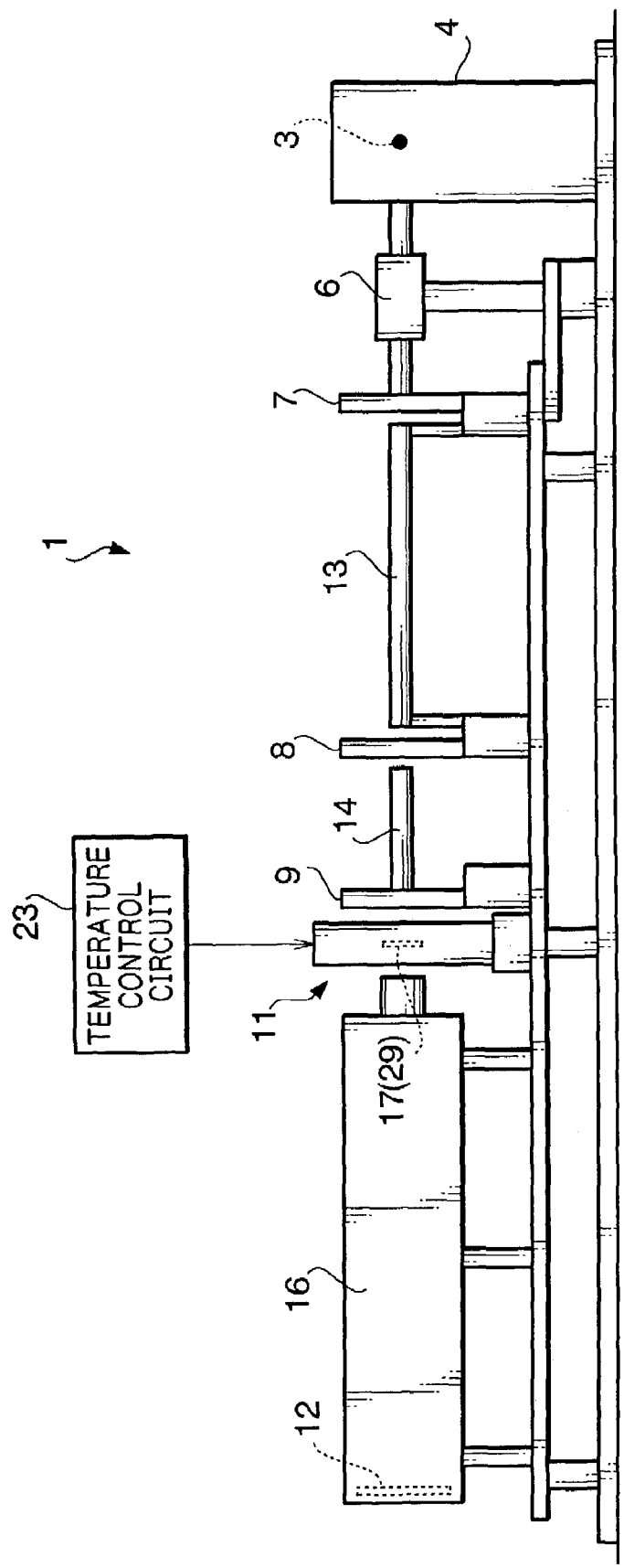
FIG. 1 is a front view of an X-ray small-angle optical device incorporated in an X-ray measuring apparatus according to the present invention.
Figure 2:
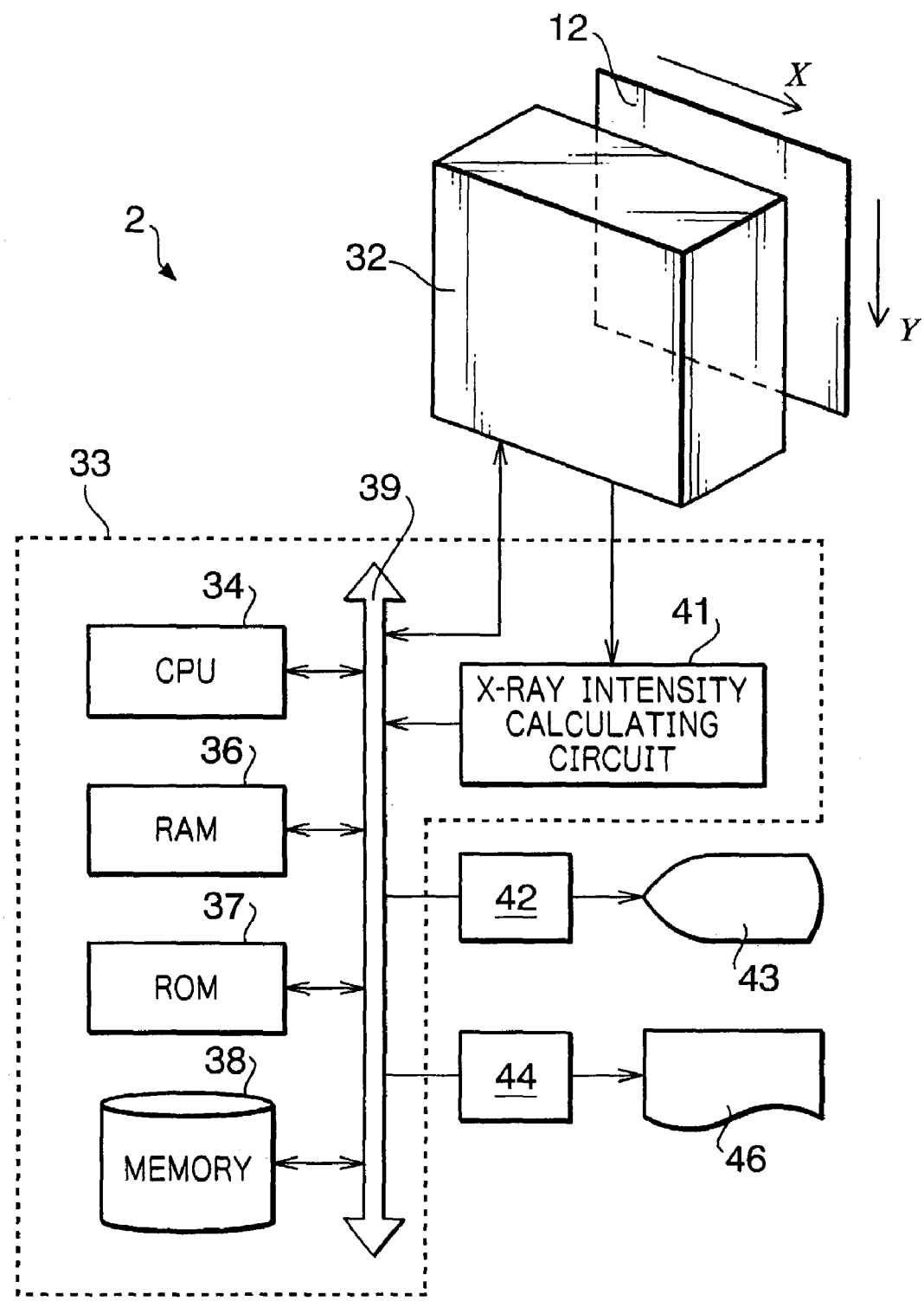
FIG. 2 is a diagram showing a reading device incorporated in the X-ray measuring apparatus according to this invention.

FIG. 1 shows an X-ray small-angle optical device 1 which is one of the components of the X-ray measuring apparatus. FIG. 2 shows a reading device 2 which is another component of the X-ray measuring apparatus. The devices 1 and 2 are installed within a small area that an operator can operate both devices without the necessity of walking a long distance. Note that the X-ray small-angle optical device 1 and the reading device 2 are nothing more than examples of devices that may be used in the present invention to evaluate the ion-exchange film. In other words, they may be replaced by any other devices in the method according to this invention.

As FIG. 1 shows, the X-ray small-angle optical device 1 comprises an X-ray tube 4, a con-focal mirror 6, a first slit 7, a second slit 8, a third slit 9, a sample holder 11, and a two-dimensional X-ray detector 12. The X-ray tube 4 comprises an X-ray source 3. The con-focal mirror 6 is the X-ray focusing means that focuses X-rays generated from the X-ray source 3 into a focal point. The two-dimensional X-ray detector 12 is a phosphor plate that has a planer storage phosphor material formed on the X-ray detecting surface.

Figure 3:
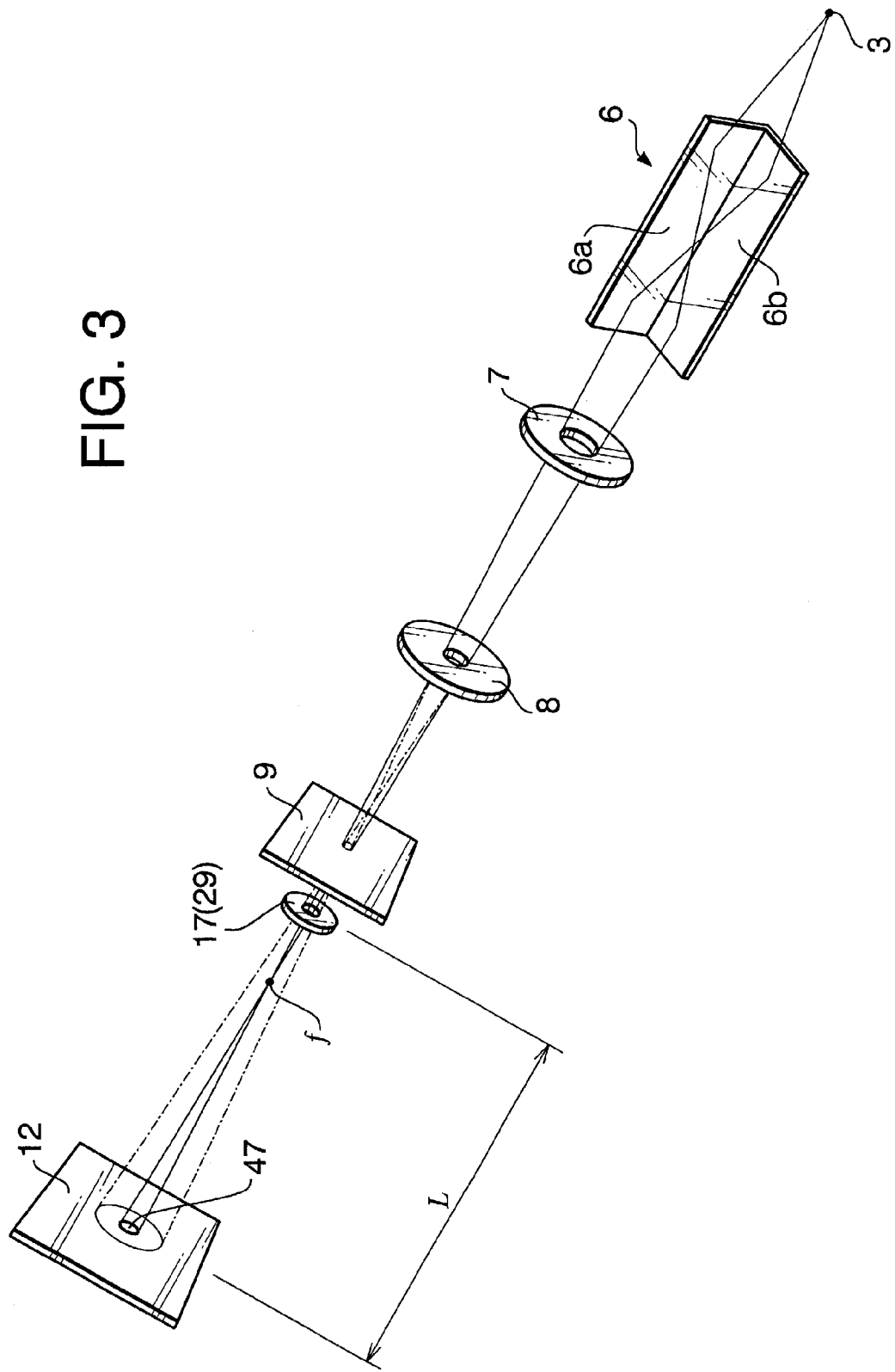
FIG. 3 is a schematic diagram illustrating how an X-ray propagates in the X-ray small-angle optical device shown in FIG. 1.

FIG. 3 is a schematic diagram illustrating how an X-ray propagates in the optical system shown in FIG. 1. In FIG. 3, the components identical to those shown in FIG. 1 are designated at the same reference numerals. As FIG. 3 shows, the con-focal mirror 6 has two X-ray reflecting surfaces 6a and 6b that intersect with each other at right angles. The mirror 6 is an X-ray reflecting mirror that is designed such that the X-rays reflected by the surfaces 6a and 6b reach the same focal point f or points f close to one another.

The con-focal mirror 6 is a single-layer mirror. It may be made of material that can reflect X-rays, such as nickel, platinum, tungsten, or the like. Alternatively, the mirror 6 may be a multi-layer mirror that has an X-ray reflecting surface and comprises a plurality of thin films laid on the reflecting surface, one upon another. In this case, the mirror 6 reflects X-rays by virtue of the diffraction of X-rays.

As seen from FIG. 1, a tube 13 is arranged between the first slit 7 and the second slit 8, and a tube 14 is provided between the second slit 8 and the third slit 9. Further, a tube 16 is arranged downstream of the sample holder 11 (namely, on the left side of FIG. 1). The two-dimensional X-ray detector 12 is set within one end of the tube 16. The tubes 13, 14 and 16 are connected to a vacuum device and depressurized to a vacuum or almost to a vacuum.

The X-ray small-angle optical device 1 of this embodiment is configured to detect the scattered radiation emanating from the sample 17 held by the sample holder 11. The scattered radiation, however, has a very small intensity. It is therefore necessary to prevent the X-rays scattered by air from disturbing the light beam emanating from the sample 17. To this end, the tubes 13, 14 and 16 are arranged as specified above, thus constituting a vacuum path.

Figure 4:
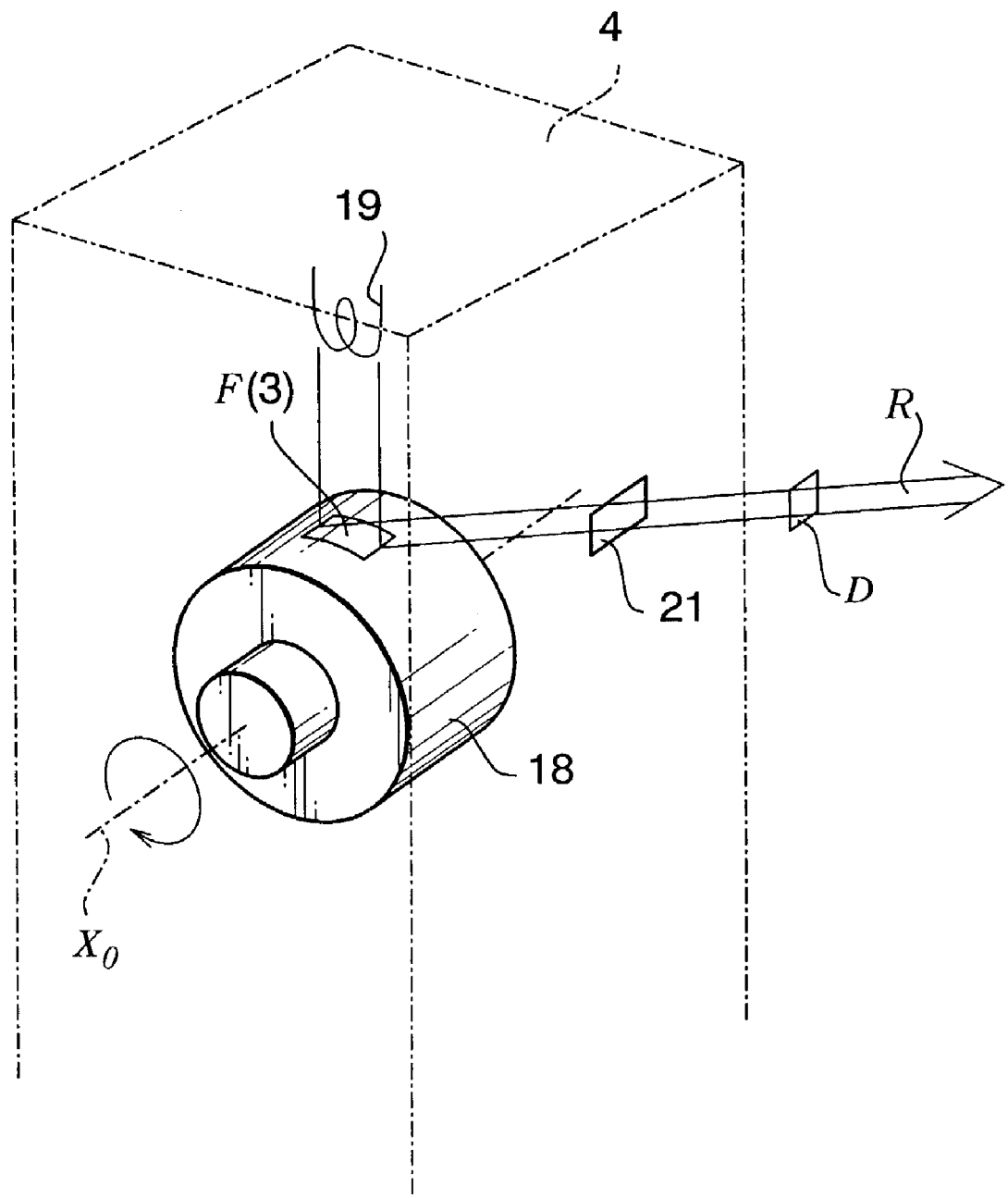
FIG. 4 is a perspective view of an X-ray source that may be used in the X-ray small-angle optical device shown in FIG. 1.

The X-ray tube 4 used in this embodiment should be one that can generate as intense X-rays as possible, so that the sample 17 may be analyzed fast. This is why the X-ray rube 4 comprises a rotor target 18 and a filament 19, as is illustrated in FIG. 4. The rotor target 18 incorporates a cooling unit and can rotate at high speed. The filament 19 can apply a high voltage between it and the target 18.

The filament 19 is heated and emits thermoelectrons when an electric current flows through it. The thermoelectrons emitted from the filament 19 are accelerated, thanks to the high voltage applied between the target 18 and the filament 19. The thermoelectrons thus accelerated impinge upon the surface of the target 18. The region in which the thermoelectrons impinge is an X-ray focus F, at which X-rays are generated. That is, the X-ray focus F is the X-ray source 3. In the present embodiment, a point-focusing X-ray is picked out from the X-ray source 3.

The X-ray focus F is rectangular as in most cases. An X-ray is acquired at a short side of the rectangular X-ray focus F in the present embodiment. More precisely, the X-ray is emitted outside the X-ray tube 4 through an X-ray window 21 located at the short side of the X-ray focus F. The X-ray R thus emitted has a cross section D that is squared, almost squared, circular, or almost circular. Since the X-ray thus emitted has such a cross section, the X-ray focus F is called "X-ray focus of point type."

The X-ray may be emitted from a long side of the rectangular X-ray focus F. In this case, the X-ray emitted has a rectangular cross section. Hence, the X-ray focus is called "X-ray focus of line type".

In the present embodiment, the X-ray tube 4 is depressurized to a vacuum or almost a vacuum and the target 18 is rotated at high speed around its axis X0. Further, cooling water is circulated in the target 18. The surface of the target 18 is cooled as the target 18 is rotated at high speed and the cooling water flows in the target 18. This helps to supply many electrons to the X-ray focus F. As a result, an X-ray of high intensity can be generated at the X-ray focus F. The surface of the target 18 may be, for example, a Cu (copper) layer.

The slits provided in the X-ray optical system shown in FIG. 1 may have various shapes, rectangular, circular (namely, pinhole), and the like. In the present embodiment, the first, second and third slits 7, 8 and 9 are pinholes as shown in FIG. 3. The pinholes are desirable slits since the X-ray source 3 generates a point-focusing X-ray and the mirror 6 is a con-focal mirror in this embodiment.

Figure 5:
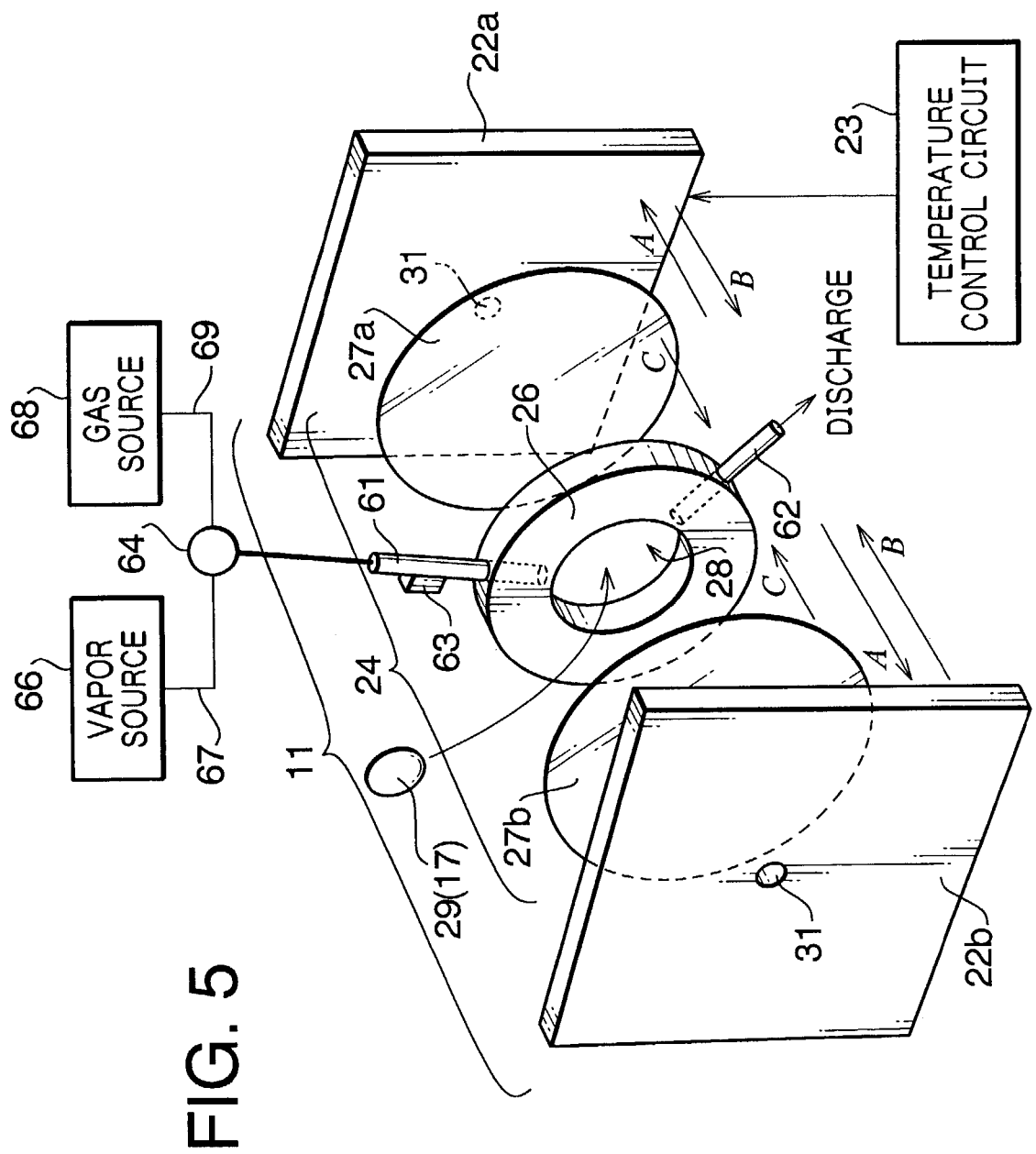
FIG. 5 is an exploded view of an internal structure of the sample holder used in the X-ray small-angle optical device shown in FIG. 1.

As FIG. 5 shows, the sample holder 11 illustrated in FIG. 1 has a pair of heat plates 22a and 22b that function as a sample-heating means. The heat plates 22a and 22b can move away from each other in the directions arrows A and toward each other in the direction of arrows B, when driven by an opening-closing mechanism (not shown). The sample-heating means is not limited to the heat plates 22a and 22b. It can be replaced by a sample-heating means of any other structure.

The heat plate 22a or the heat plate 22b, or both contain a member that generates heat when an electric current flows through it. The heat-generating member is, for example, an electric heating wire. The heat-generating member is connected to a temperature control circuit 23. The circuit 23 controls the current supplied to the heat-generating member, thus changing the amount of heat that the heat plate 22a or the heat plate 22b, or both generate. Note that the heat plate 22a or the heat plate 22b, or both have an inner surface that radiates heat.

The heat plates 22a and 22b clamp a sample chamber assembly 24, with their inner surfaces (i.e., heat-radiating surfaces) set in direct contact with the sample chamber assembly 24. Preferably, the heat plates 22a and 22b firmly hold the assembly 24 by using an elastic bias means such as springs, thus preventing the sample chamber assembly 24 from moving.

The sample chamber assembly 24 has a ring-shaped thick member 26 and shields 27a and 27b. The shields 27a and 27b are adhered to the sides of the thick member 26. The thick member 26 is made of, for example, brass and has a thickness of, for example, about 1 mm. The shields 27a and 27b are flexible films and made of material that is transparent to X-rays and exhibits a great mechanical strength. The material may be, for example, polyethylene terephthalate such as Myler (trade name), polyimide such as Kapton (trade name), or the like. In FIG. 5, the shields 27a and 27b are presented as discs. Nonetheless, they may be rectangular instead, or may have any other desirable shape.

The shields 27a and 27b are of the type that adheres to the thick member 26 when they are pressed onto the thick member 26 in the direction of arrows C. The shields 27a and 27b may be bonded to the surface of the thick member 26 by applying appropriate adhesive. Once the shields 27a and 27b are adhered to the sides of the thick member 26, a sample chamber 28 is provided. The sample chamber 28 is airtight and shielded from outside.

A gas-introducing pipe 61 has one end inserted in a hole made the thick member 26 and opening at the outer and inner circumferential surfaces of the thick member 26. The gas-introducing pipe 61 opens outside the sample chamber 28. Thus, the pipe 61 connects the sample chamber 28 to the outside of the thick member 26. A humidity sensor 63 is provided on the gas-introducing pipe 61.

The humidity sensor 63 detects the humidity of the gas flowing through the gas-introducing pipe 61 and generates an electric signal that represents the humidity detected. The output signal of the humidity sensor 63 may be input to a display, such as a CRT (namely, Cathode Ray Tube) or a flat-panel display, which displays the humidity in the form of a numerical value. Alternatively, the output signal of the humidity sensor 63 may be used as a reference value for controlling the humidity of the gas flowing through the gas-introducing pipe 61.

The gas-introducing pipe 61 is connected, at the other end, to a gas mixer 64, which has two input ports. The first input port is connected to a vapor source 66 by a pipe 67. The second input port is connected to a gas source 68 by a pipe 69. The gas mixer 64 is designed to mix the vapor supplied from the vapor source 66 and the gas supplied from the gas source 68. The gas is, for example, nitrogen ($N_2$). The mixture gas prepared in the mixer 64 is sent into the sample chamber 28 through the gas-introducing pipe 61. The mixture gas, which has some humidity, is discharged from the sample chamber 28 through a gas exhaust pipe 62.

The gas mixer 64 incorporates a valve. The valve is controlled, adjusting the mixing ratio between the vapor and the gas. This controls the humidity of the gas supplied into the sample chamber 28 via the gas-introducing pipe 61. The valve in the gas mixer 64 may be controlled by manipulating a dial provided on the gas mixer 64. Alternatively, it may be remote-controlled by operating a dial located remote from the body of the gas mixer 64.

Before both shields 27a and 27b are adhered to the thick member 26, an ion-exchange film 29, or sample 17, is placed in the sample chamber 28 in the present embodiment. Then, the shields 27a and 27b are adhered to the thick member 26, thus closing the sample chamber 28. Note that the ion-exchange film 29, which is used as sample 17, is a part of the ion-exchange film to be used in a fuel cell, which is larger and shaped differently.

After the ion-exchange film 29 is placed in the sample chamber 28 and the chamber 28 is closed with the shields 27a and 27b, the gas is introduced into the sample chamber 28 through the gas-introducing pipe 61. Thus, the ion-exchange film 29 is set at the humidity of the gas. In this embodiment, the vapor source 66, gas source 68 and gas mixer 64 constitute a humidity-controlling means.

The ion-exchange film 29 may be used as a component of a fuel cell. If this is the case, the ion-exchange film 29 remains wet. It is therefore important to determine how the properties of the film 29 change as the film 29 is gradually moistened from the dried state to the fully wetted state (namely, humidity of 100%). The changes in the properties of the film 29 can be determined by the above-mentioned humidity-controlling means that is associated with the sample chamber 28.

The sample chamber assembly 24 that defines the sample chamber 28 is clamped between the heat plates 22a and 22b. Hence, the air in the chamber 28 is heated as the plates 22a and 22b radiate heat. The ion-exchange film 29 placed in the chamber 28 is therefore heated.

When used as a component of a fuel cell, the ion-exchange film 29 is heated as an electrochemical reaction proceeds in the fuel cell. Thus, the heat plates 22a and 22b can heat the ion-exchange film 29 to any desirable temperature or to the very temperature at which it is actually used in the fuel cell. If used in a fuel cell, the ion-exchange film 29 may be heated to a temperature ranging from room temperature to 100° C. The heat plates 22a and 22b constitute a heating means. The heating means can set the ion-exchange film 29 at any desirable temperature in the sample chamber 28.

The heat plates 22a and 22b have a through hole 31 each, in their center parts. One of the holes 31 allows passage of the X-rays being applied to the ion-exchange film 29. The other hole 31 allows passage of the scattered radiation emanating from the ion-exchange film 29.

The reading device 2 shown in FIG. 2 has a reading unit 32 and a processing unit 33. The reading unit 32 scans an object with, for example, a laser beam, in X direction (i.e., main scanning direction) and Y direction (i.e., sub-scanning direction). That is, the unit 32 excites the object, or the storage phosphor plate 12, with the laser beam, thereby reading an energy latent image from the storage phosphor plate 12.

The processing unit 33 has a CPU (i.e., Central Processing Unit) 34, a RAM (i.e., Random Access Memory) 36, and a ROM (i.e., Read Only Memory) 37. The CPU 34 functions as a control unit and operation unit. The RAM 36 serves as a temporary storage area such as a temporary file or the like. The ROM 37 works as a storage area for fixed data that need not be altered at all. A bus 39 connects the CPU 34, RAM 36 and ROM 37 to one another, which is an address bus or a data bus.

The processing unit 33 has a memory 38 which comprises an external storage medium such as a hard disk or a CD (i.e., Compact Disc). The memory 38 has various storage areas, including a storage area for storing the program software that is used to read data. The output terminal of the reading unit 32 is connected to an X-ray intensity calculating circuit 41.

The X-ray intensity calculating circuit 41 receives a signal output from the reading unit 32. In accordance with the signal the circuit 41 finds the intensity of the X-rays that have served to form the energy latent image on the storage phosphor plate 12. The CPU 34 monitors, at all times, the coordinate position on the storage phosphor plate 12, at which the reading unit 32 is reading data from the plate 12. The CPU 34 and the X-ray intensity calculating circuit 41 cooperate, calculating the scattering angle and intensity of the scattered radiation emanating from the sample 17 shown in FIG. 3, i.e., ion-exchange film 29, from the latent image data stored in the storage phosphor plate 12.

Referring again to FIG. 2, an image display 43 and a printer 46 are connected to the processing unit 33 by a video data generating circuit 42 and a print data generating circuit 44, respectively. The image display 43 may be a CRT (i.e., Cathode Ray Tube) display, a flat panel display, or the like. The flat panel display may be a planar display such as a liquid crystal display, EL (i.e., Electro Luminescence) display, a plasma display, or the like. The printer 46 may be one selected from various types including an ink-coating type, an electrostatic transfer type, and the like.

A method of evaluating organic samples, or ion-exchange film, which employs the X-ray measuring apparatus described above, will be explained. In the present embodiment, the ion-exchange film 29 is evaluated, by changing the humidity ambient to the film 29 from 0% (i.e., drying film 29) to 100% (i.e., wetting film 29).

How the film 29 is evaluated while remaining dried will be described first. Referring now to FIG. 5, the ion-exchange film 29 is placed in the sample chamber 28 of the sample chamber assembly 24. The heat plates 22a and 22b are moved, clamping the sample chamber assembly 24. The ion-exchange film 29 is thereby held at a prescribed position in the sample chamber assembly 24. Then, the gas supplying into the sample chamber 28 is stopped or drying gas is supplied into the sample chamber 28, thus drying the ion-exchange film 29 in the sample chamber 28.

The method of evaluating organic samples was carried out when the room temperature was 25° C. The temperature in the sample chamber 28 was first set at 80° C. and then changed to 120° C., 150° C., 200° C., 230° C., 270° C., 300° C., and finally to 330° C.

The sample was evaluated at each of the temperatures specified above, by means of the X-ray small-angle optical device 1 and reading device 2 shown in FIG. 1 and FIG. 2, respectively. More precisely, the X-ray source 3 was driven and emitted an X-ray. The X-ray was applied to the ion-exchange film 29. Irradiated with the X-ray, the film 29 generated scattered radiation. The scattered radiation irradiated the storage phosphor plate 12. Irradiated with the radiation, the storage phosphor plate 12 stored an energy latent image.

To be more specific, the X-ray source 3 emits an X-ray of high intensity, which is point-focused. The con-focal mirror 6 focuses the X-ray at the focus f. The first slit 7 and second slit 8, which constitute a double slit, render the focused X-ray stable. The third slit 9 prevents the parasitic scattered radiation generated at the second slit 8 from irradiating the ion-exchange film 29 or the storage phosphor plate 12.

Figure 6:
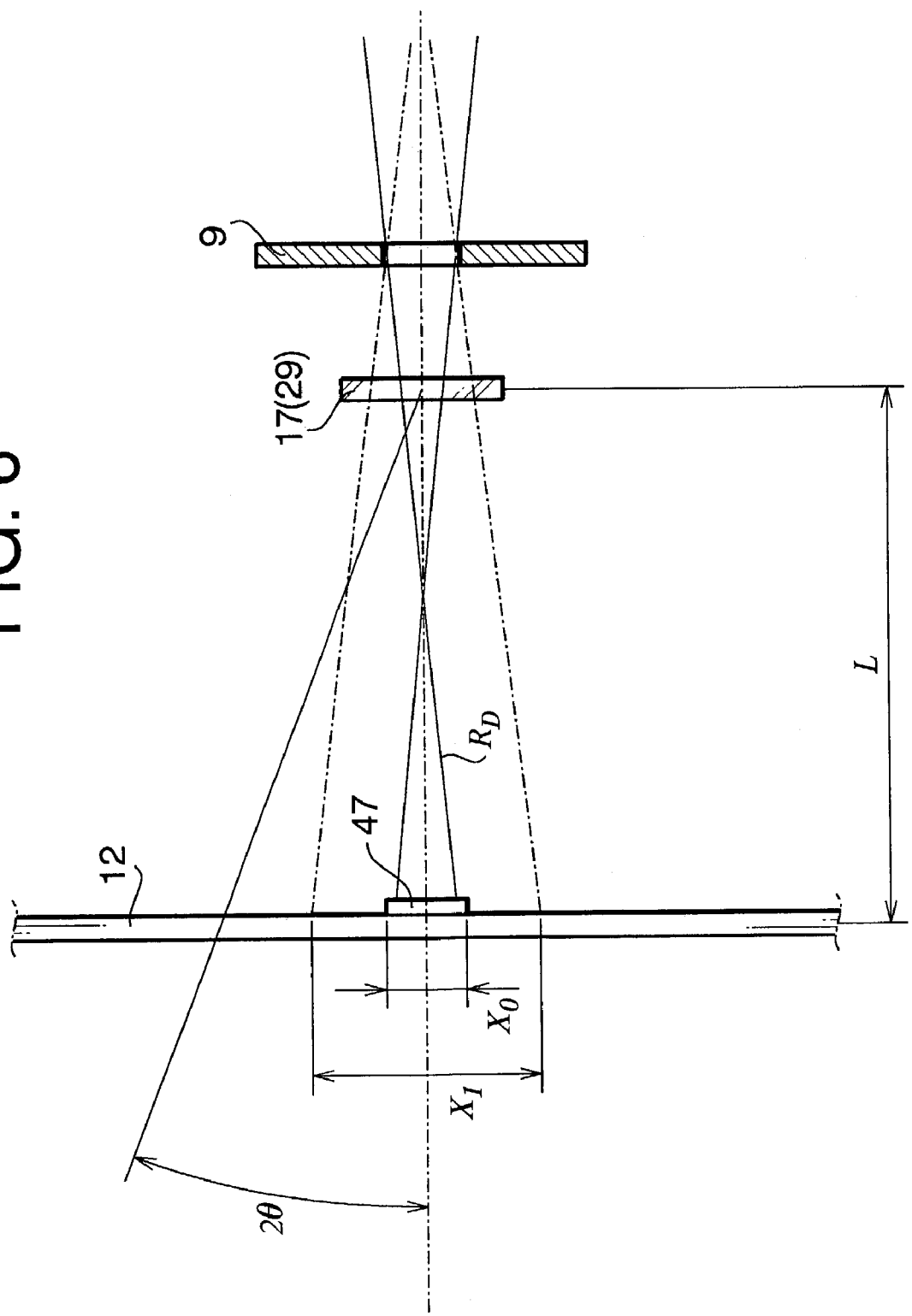
FIG. 6 is a schematic diagram illustrating how the two-dimensional X-ray detector is exposed to scattered radiation in the X-ray small-angle optical device shown in FIG. 1.

The X-rays passes through the third slit 9 and is applied to the ion-exchange film 29. Then, radiation scattered at an angle $2\theta$ that determined by the molecular structure of the film 29 is generated as shown in FIG. 6. The scattered radiation has intensity that depends on the molecular structure of the ion-exchange film 29. An energy latent image corresponding to the intensity of the scattered radiation is stored in that part of the storage phosphor plate 12 which has been irradiated with the scattered radiation.

As shown in FIG. 6, a direct beam stopper 47 is mounted on the region X0 of the storage phosphor plate 12, toward which a direct beam $R_D$ is applied. The stopper 47 prevents the direct beam $R_D$ from directly illuminating the storage phosphor plate 12. In FIG. 6, "X1" denotes the region in which the parasitic scattered radiation generated at the second slit 8 reaches the storage phosphor plate 12, not blocked by the third slit 9.

In the regions X0 and X1 of the storage phosphor plate 12, the scattered radiation from the ion-exchange film 29 cannot be measured, bothered by the direct beam and the parasitic scattered radiation. Hence, the region of small angle ($2\theta$), where the X-ray small-angle optical device 1 according to this embodiment can measure X-rays, lies outside the region X1 of FIG. 6. The small angle ranges from 0.1° to 5°, or from 0.1° to 4°.

To measure scattered radiation in such a small-angle region, it is necessary to narrow the slits 7, 8 and 9, thereby to render the X-ray extremely thin, and to lengthen the camera length L. In view of the above, the ordinary X-ray measuring method using a wide-angle goniometer cannot measure the X-ray. Since the X-ray is made thin, it has low intensity when it reaches the ion-exchange film 29. It therefore takes a long time to measure the X-ray.

In the present embodiment, the con-focal mirror 6 focuses the X-ray emitted from the X-ray source 3 as illustrated in FIG. 3. Moreover, the X-ray from the X-ray source 3 is a point-focused one. That is, the X-ray applied to the ion-exchange film 29 is more intense than in the conventional X-ray measuring apparatus. With this embodiment it is possible to apply scattered radiation of sufficient intensity to the storage phosphor plate 12, within a short time, for example about 20 minutes. In other words, the X-ray measuring apparatus according to the embodiment can measure the X-ray within such a short time.

Figure 9A:
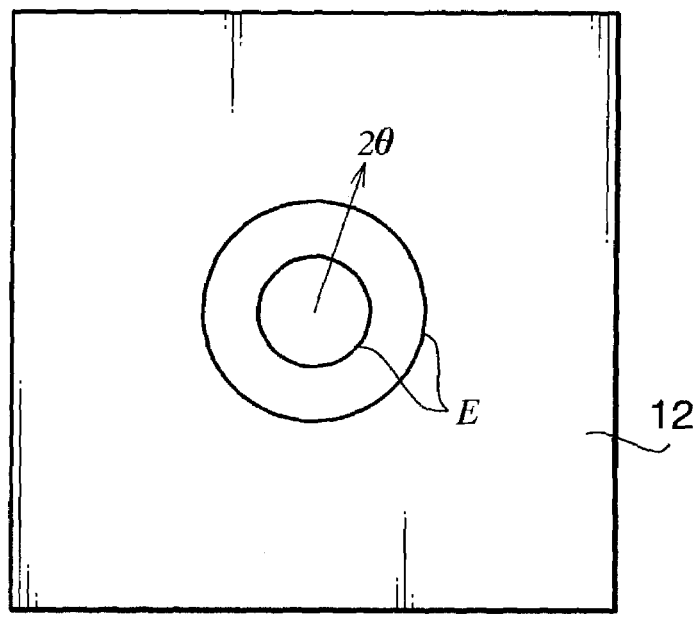
FIG. 9A is a diagram depicting a two-dimensional scattering profile formed on the two-dimensional X-ray detector when the molecular structure of the sample has disturbance.
Figure 9B:
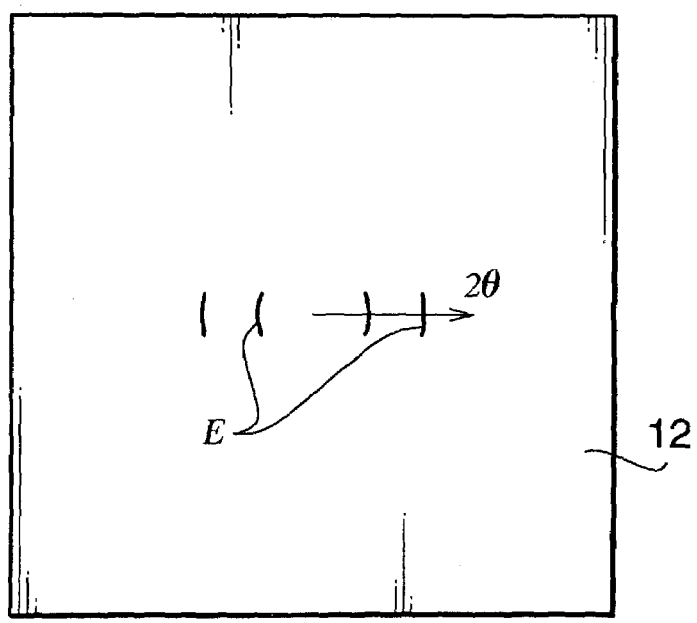
FIG. 9B is a diagram depicting a two-dimensional scattering profile formed on the two-dimensional X-ray detector when the molecular structure of the sample has no disturbance.

When the small-angle scattered radiation is measured at one temperature, such a two-dimensional scattering profile E as depicted in FIG. 9A or FIG. 9B is formed on the storage phosphor plate 12, as an energy latent image.

The image display 43 or the printer 46, either shown in FIG. 2 displays the two-dimensional scattering profile E. The profile E displayed or printed is examined to evaluate the ion-exchange film 29. Thus, it is possible to evaluate the regularity of molecular structure, more precisely the alignment of the straight chains 54 and side chains 56 in each molecule.

As described above with reference to FIG. 1 and FIG. 3, a latent image pertaining to the ion-exchange film 29 is formed in the storage phosphor plate 12 by exposing the plate 12 to the scattered radiation at one of measuring temperatures. Then, the storage phosphor plate 12 is removed from the X-ray small-angle optical device 1 and set at a reading position prescribed with respect to the reading unit 32 of the reading device 2 shown in FIG. 2. The reading unit 32 scans the surface of the storage phosphor plate 12, measuring the scattering angle (2θ) and intensity of the scattered radiation from the two-dimensional scattering profile E shown in FIG. 9.

Figure 8:
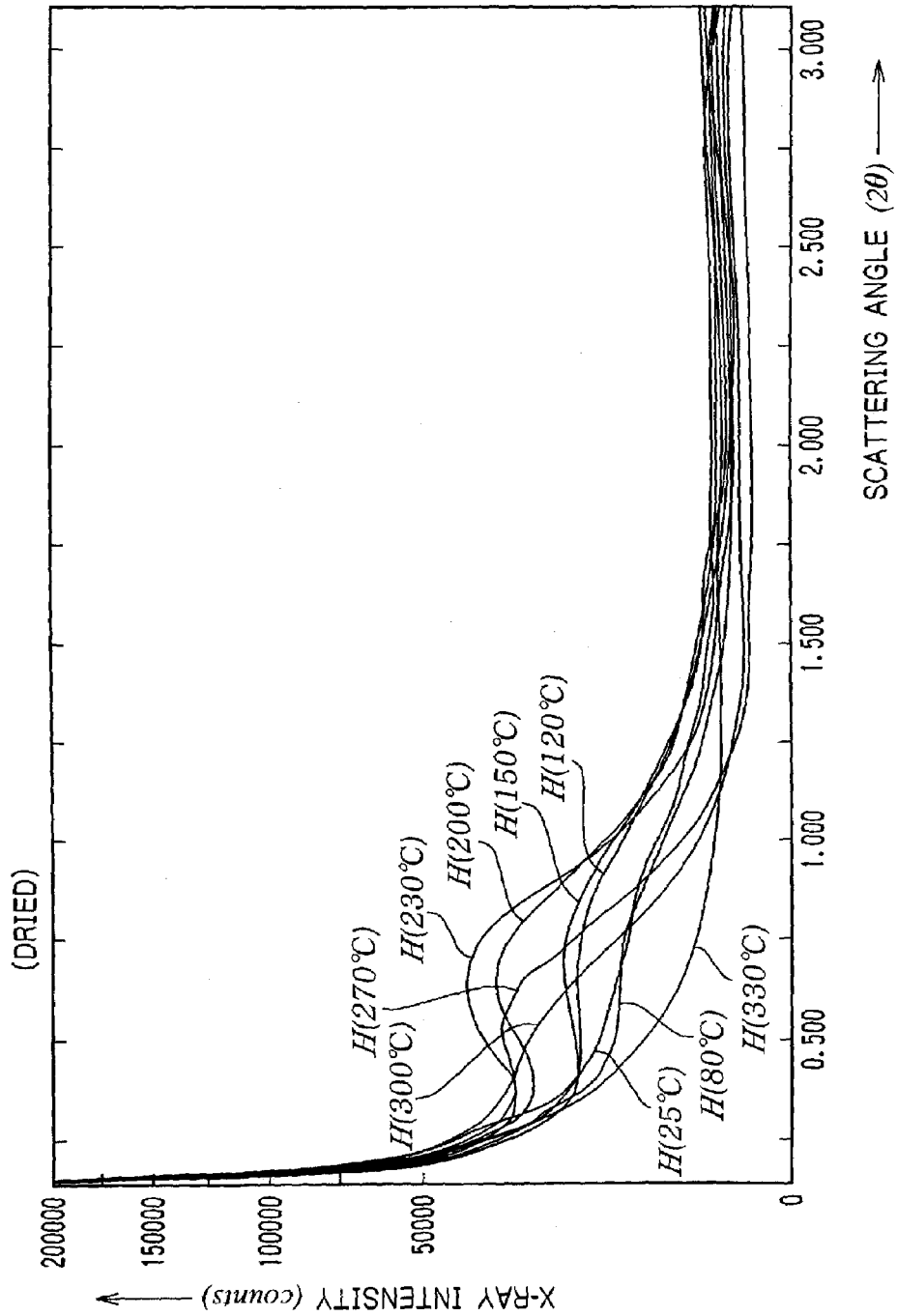
FIG. 8 is a graph representing another small-angle scattering curves read by the reading device shown in FIG. 2.

The CPU 34 shown in FIG. 2 stores the scattering angel (2θ) and intensity of the scattered radiation, thus measured, at a predetermined storage area in the RAM 36 or memory 38, in the form of, for example, a data table. The image display 43 and the printer 46 can display and print the data table, as such a small-angle scattered-radiation graph H as shown in FIG. 8. In the graph H, the scattering angle (2θ) is plotted on the abscissa, and the X-ray intensity on the ordinate.

Assume that the ion-exchange film 29 is examined, while held as shown in FIG. 1 at room temperature (i.e., 25° C.). Then, we have the small-angle scattering curve H(25° C.) illustrated in FIG. 8. Next, the temperature of the ion-exchange film 29 is changed to 80° C., 120° C., 150° C., 200° C., 230° C., 270° C., 300° C., and 330° C., by the control of the temperature control circuit 23 shown in FIG. 1, and the ion-exchange film 29 is examined at these temperatures by the X-ray small-angle optical device 1. As a result, the two-dimensional scattering profile E shown in FIG. 9 is formed in the storage phosphor plate 12. The reading device 2 reads the scattering profile E from the plate 12. The CPU 34 processes the data representing the scattering profile E, generating the data items that represent the small-angle scattering curves H(80° C.), H(120° C.), H(150° C.), H(200° C.), H(230° C.), H(270° C.), H(300° C.) and H(330° C.), all shown in FIG. 8.

Figure 11:
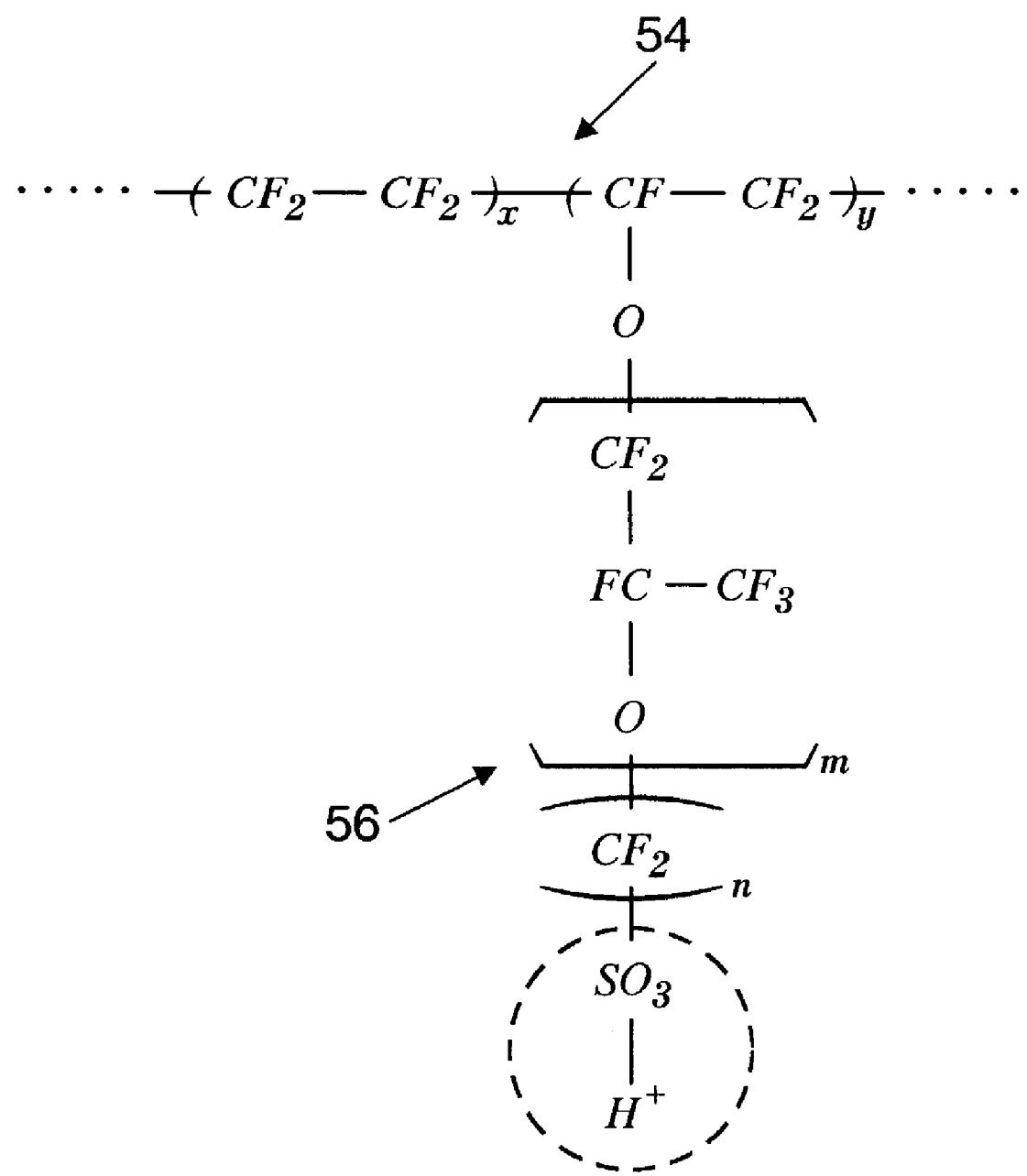
FIG. 11 is a structural formula of the ion-exchange film.
Figure 12:
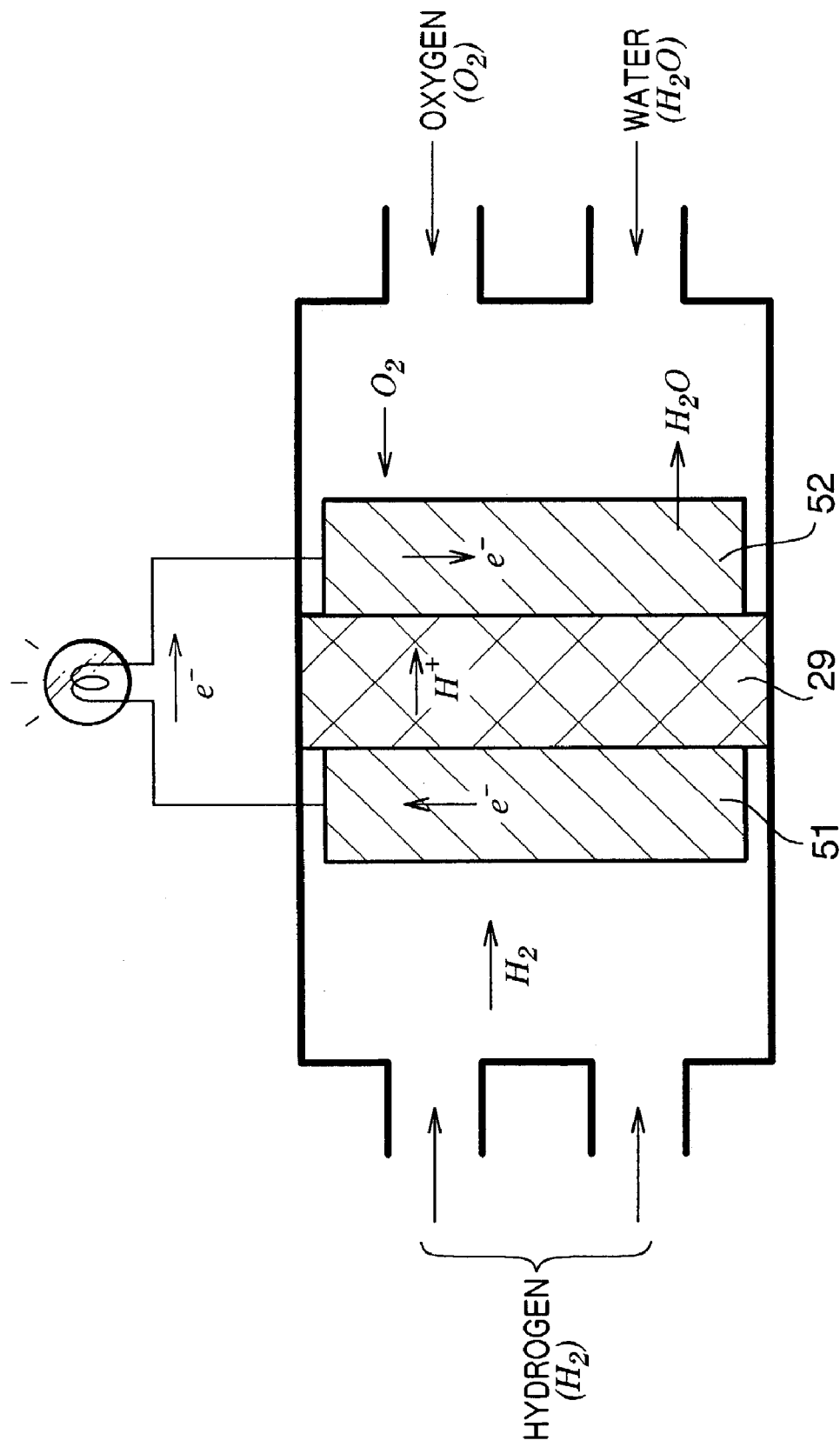
FIG. 12 is a schematic representation of a fuel cell using the ion-exchange film.

Any person who observes the graph of FIG. 8 can recognize the peaks on these small-angle scattering curves H and can read the X-ray intensities at the peaks. The positions of the peaks and the X-ray intensities at the peaks can be attributed to the changes that the ion-exchange film 29 undergoes in terms of molecular structure (as shown in FIG. 10C and FIG. 11) as its temperature changes while it remains dry. Thus, the observer of the graph of FIG. 8 can determine the molecular structure that the film 29 has while it remains dry, from the changes in the positions of the peaks, the changes in the X-ray intensities at the peaks, or both of them.

How the ion-exchange film 29 is evaluated while remains wetted, or set at the humidity of 100%, will be explained. To set the film 29 at the humidity of 100%, the gas mixer 64 is operated, taking a great amount of vapor from the vapor source 66. The gas mixer 64 introduces all vapors into the sample chamber 28. The humidity in the sample chamber 28 is thereby set at 100%.

Experiments were conducted at the room temperature of 26° C. to perform the method of evaluating the ion-exchange films, according to the present embodiment. The heat plates 22a and 22b were heated, changing the temperature of the ion-exchange film 29 held in the sample chamber 28 to 50° C., 60° C., 70° C., 80° C., 90° C., 100° C., 110° C., 120° C. and 130° C.

The small-angle X-ray optical device 1 and the reading device 2, shown in FIG. 1 and FIG. 2, respectively, were used to evaluate the ion-exchange film 29 at various temperatures. As a result, small-angle scattering curves G, all shown in FIG. 7, were obtained at the respective temperatures specified above. These curves were obtained when the evaluation condition was changed while the ion-exchange film 29 remained wet, whereas the curves H shown in FIG. 8 were obtained when the condition was changed while the film 29 remained dry.

In the present embodiment, the small-angle scattering curves obtained while the film 29 remained dry (i.e., humidity of 0%) are compared with those obtained while the film 29 remained wet (i.e., humidity of 100%). Nonetheless, the mixing ratio of vapor to the gas may be adjusted, if necessary, in the gas mixer 64 shown in FIG. 5. Then, the humidity in the sample chamber 28 can be set at any desired value other than 0% and 100%. This makes it possible to determine the molecular structure that the ion-exchange film 29 has while remaining at any desired humidity.

The condition in which the ion-exchange film 29 can fully perform its function can be determined even if it has yet to be wetted, by comparing the position of the peak for a particular temperature and the X-ray intensity at the peak. The condition thus determined contributes to downsizing of the fuel cell.

The CPU 34 shown in FIG. 2 calculates peaks P at the temperatures specified above, respectively, from the small-angle scattering curves G(26° C.) to G(130° C.), for the scattering angle (2θ). The CPU 34 calculates the X-ray intensities at these peaks from the intensities that the scattered radiation has at the temperatures specified above. The CPU 34 causes the image display 43 or the printer 46 to display or print the peak P at each temperature, on the corresponding small-angle scattering curve G, in such a dot-matrix form as is illustrated in FIG. 7.

Figure 7:
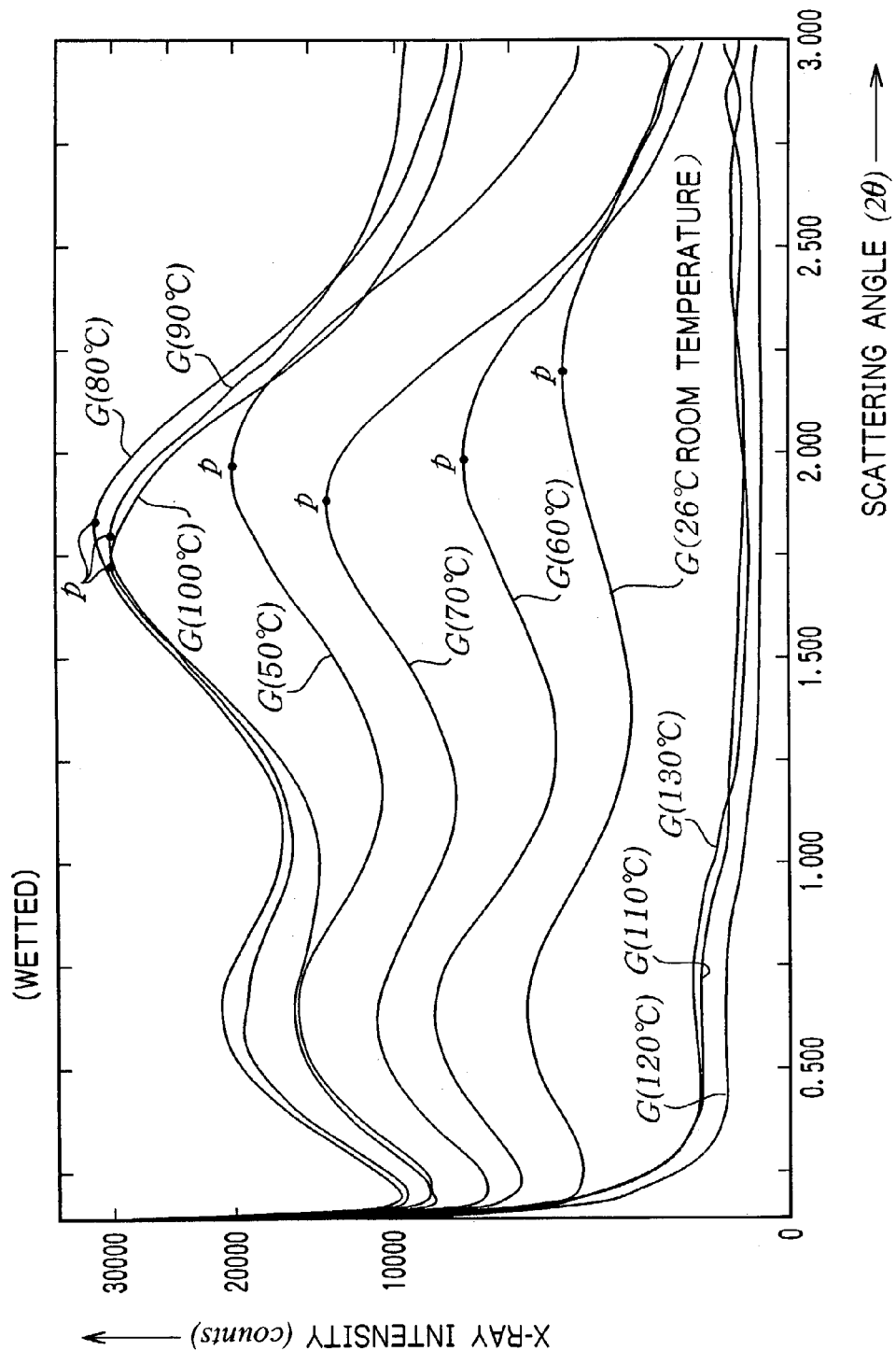
FIG. 7 is a graph representing small-angle scattering curves read by the reading device shown in FIG. 2.

Any person who observes the graph of FIG. 7 can easily recognize how the position of the peak changes and how the X-ray intensity at the peak changes as the temperature of the ion-exchange film 29 is varied while the film 29 remains at the humidity of 100%. The peak position and the X-ray intensity at the peak change as the molecular structure of the ion-exchange film 29, shown in FIG. 10C and FIG. 11, changes due to the change in the temperature of the film 29 maintained at the humidity of 100%. Thus, the observer can determine the molecular structure of the ion-exchange film 29 by evaluating the change in the position of the peak on the small-angle scattering curve G (as shown in FIG. 7) or the change in the X-ray intensity at the peak, or both.

Once incorporated into a fuel cell, the ion-exchange film 29 is used at a temperature ranging from room temperature to a higher temperature but less than 100° C. It is used most frequently at 80° C. to 90° C. The molecular structure that the ion-exchange film 29 has while it is acting in the fuel cell can be determined by referring to the small-angle scattering curves G(80° C.) and G(90° C.), both presented in FIG. 7. In other words, the performance of the ion-exchange film 29, thus measured, can be evaluated when it is used in practice by referring to the small-angle scattering curves G(80° C.) and G(90° C.).

The inventors hereof believe that, if the positions of the peaks on the small-angle scattering curves G shown in FIG. 7 are known, the molecular structure of the ion-exchange film 29 can be determined. If the X-ray intensities at the peaks are known, the number of side chains 56 and the regularity of the molecular structure of the ion-exchange film 29 can be determined.

As may be clear from the foregoing, the X-ray measuring apparatus comprising the X-ray small-angle optical device 1 (as shown in FIG. 1) and the reading device 2 (as shown in FIG. 2) can accurately evaluate the performance, for example, ion-exchanging ability, of the ion-exchange film 29 in the condition of actual use. Thus, the method according to this embodiment can evaluate ion-exchange films set in such a use condition, whereas the conventional method, such as NMR-measuring method and IR-measuring method, can hardly evaluate ion-exchange film set in the use condition.

In particular, according to this embodiment, the X-ray source 3 provided in the X-ray small-angle optical device 1 (as shown in FIG. 1) can emit X-rays of high intensity. This is because the X-ray source 3 comprises a rotor target that incorporates a cooling unit. Further, the con-focal mirror 6 focuses the X-ray, which irradiates the ion-exchange film 29. Therefore, the small-angle scattering measuring can be performed on the ion-exchange film 29 within a very short time.

The ion-exchange film 29 is maintained in wetted state and at a high temperature close to 100° C. If it takes a long time to perform the small-angle scattering measuring, the state of the ion-exchange film 29 and the humidity ambient to the film 29 will change before the measuring is finished. This may render it no longer possible to achieve a reliable in-situ measuring. To perform a reliable in-situ measuring, the X-ray applied to the ion-exchange film 29 is intensified in this embodiment, shortening the measuring time. Thus, a high-precision in-situ measuring is accomplished in the present embodiment.

Second Embodiment

In the first embodiment described above, the performance of the ion-exchange film 29 is evaluated from three factors, i.e., the difference between the positions of the peaks on the small-angle scattering curves G and H, the difference between the X-ray intensities at these peaks, and the two-dimensional scattering profiles E shown in FIG. 9. In the second embodiment of the invention, the performance of the film 29 can be evaluated on the basis of only one or two of the three factors.

Third Embodiment

In the embodiments described above, one ion-exchange film 29 is set in different conditions, the small-angle scattering curves G and two-dimensional scattering profiles E for the respective conditions are obtained, and the change in the molecular structure of the ion-exchange film 29 is determined, thus evaluating the performance of the film 29.

Instead, a plurality of ion-exchange films whose molecular structures are unknown are subject to X-ray, small-angle measuring in the third embodiment of the present invention. Small-angle scattering curves G and H and two-dimensional scattering profiles E are thereby obtained. From the curves G and H and the profiles E, the different molecular structures of the respective ion-exchange films can be determined. In the third embodiment, the ion-exchange films can be measured while maintained at the same temperature.

Moreover, the small-angle scattering curves G and H for a standard ion-exchange film may be stored in the memory 38 of the processing unit 33 shown in FIG. 2 and may be compared with the small-angle scattering curves G and H actually obtained of an ion-exchange film. Thus, the ion-exchange film is evaluated in terms of its performance.

Fourth Embodiment

In the embodiments described above, the X-ray source is a point-focus source that comprises a rotor target and the con-focal mirror is used as X-ray focusing means. The fourth embodiment may use an X-ray focusing means other than a con-focal mirror, or may not use an X-ray focusing means at all as the case may be. Further, a line-focus X-ray source may be used in some cases. Still further, a target other than a rotor target may be used in some cases.

Furthermore, a monochromator may be arranged on the X-ray path extending from the X-ray source 3 to the ion-exchange film 29, preferably on the X-ray path extending from the X-ray source 3 to the con-focal mirror 6. Thus, the X-ray being applied to the ion-exchange film 29 is changed to a monochromic beam, such as a CuKa beam. Alternatively, the X-ray focusing means equivalent to the con-focal mirror 6 may be a monochromator made of single crystal. If this is the case, it can focus the incident X-ray and change the same to a monochromic beam at the same time.

Fifth Embodiment

In the embodiments described above, the object to be evaluated is an ion-exchange film. The fifth embodiment is designed to evaluate organic samples other than ion-exchange films. The samples that the fifth embodiment may evaluate are, for example, macromolecular organic materials, genome pharmaceutical substances, and the like.

Sixth Embodiment

The embodiments described above use an optical system having three slits as shown in FIG. 1. The sixth embodiment of the invention may use an X-ray small-angle optical device of any other configuration. Moreover, the sixth embodiment may comprise a sample holder that differs in structure from the sample holder 11 shown in FIG. 5.

In addition, various embodiments of the present invention have been described. Nevertheless, this invention is not limited to them. Rather, various changes and modifications can be made, within the scope of the claims set forth hereinafter.

What is claimed is:

1. A method of evaluating the performance of an ion-exchange film, comprising the steps of:
setting humidity ambient to ion-exchange film at any desired value separately from temperature of the ion-exchange film;
obtaining small-angle scattering curves in each of two angle ranges for the ion-exchange film at different humidities, by means of an X-ray measuring apparatus which is configured to detect X-rays scattered at small angles with respect to the axis of an X-ray applied to the ion-exchange film, said small angles include a first angle in a first angle range of $0.1° \leqq 0.88°$ in terms of an angle $2\theta$ and a second angle in a second angle range of $0.88° \leqq 5°$ in terms of the angle $2\theta$;
obtaining each small-angle scattering curve while the film remains in a different condition of humidity;
analyzing small-angle scattering curves having peaks, one of which is in the first $2\Theta$ angle range of $0.1°$ to $0.88°$ and another of which is in the second $2\Theta$ angle range of $0.88°$ to $5°$, thereby to evaluate the performance of the ion-exchange film,
wherein the step of obtaining small-angle scattering curves has a step of obtaining a two-dimensional scattering profile pertaining to the ion-exchange film, by using a two-dimensional X-ray detector; and
the X-ray measuring apparatus has a con-focal mirror which is arranged on a propagation path of the X-ray applied to the ion-exchange film and a point-focus X-ray source.

2. The method according to claim 1, wherein the step of setting humidity ambient to the ion-exchange film is carried out by inserting the ion-exchange film into a sample chamber and applying gas having humidity into the sample chamber.

3. A method of evaluating the performance of an organic sample, comprising the steps of:

setting humidity ambient to the organic sample at any desired value separately from temperature of the organic sample;

obtaining small-angle scattering curves in each of two angle ranges for the organic sample at different humidities, by means of an X-ray measuring apparatus which is configured to detect X-rays scattered at small angles with respect to the axis of an X-ray applied to the organic sample, said small angles include a first angle in a first angle range of $0.1°\leqq 0.88°$ in terms of an angle $2\theta$ and a second angle in a second angle range of $0.88°\leqq 5°$ in terms of the angle $2\theta$;

obtaining each small-angle scattering curve while the organic sample remains in a different condition of humidity; and analyzing small-angle scattering curves having peaks one of which is in the first $2\Theta$ angle range of $0.1°$ to $0.88°$ and another of which is in the second $2\Theta$ angle range of $0.88°$ to $5°$, thereby to evaluate the performance of the organic samples, wherein the step of obtaining small-angle scattering curves has a step of obtaining a two-dimensional scattering profile pertaining to the organic sample, by using a two-dimensional X-ray detector; and the X-ray measuring apparatus has a con-focal mirror which is arranged on a propagation oath of the X-ray applied to the organic sample and a point-focus X-ray source.

4. The method according to claim 3, wherein the step of setting humidity ambient to the organic sample is carried out by inserting the organic sample into a sample chamber and applying gas having humidity into the sample chamber.

* * * * *